(12) United States Patent
Palumbo et al.

(10) Patent No.: US 6,406,464 B1
(45) Date of Patent: Jun. 18, 2002

(54) ADHESIVE FAECAL COLLECTOR WITH OPTIMAL APERTURE

(75) Inventors: Gianfranco Palumbo, Bad Homburg; Vincenzo D'Acchioli, Kelkheim am Taunus, both of (DE); Peter Coles, Francavil.al Mare, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/445,931

(22) PCT Filed: Jun. 26, 1998

(86) PCT No.: PCT/US98/13369

§ 371 (c)(1),
(2), (4) Date: Dec. 20, 1999

(87) PCT Pub. No.: WO99/00089

PCT Pub. Date: Jan. 7, 1999

(30) Foreign Application Priority Data

Jun. 28, 1997 (EP) .............................. 97110602
Jun. 28, 1997 (EP) .............................. 97110603
Jun. 28, 1997 (EP) .............................. 97110604

(51) Int. Cl.$^7$ .............................. A61F 5/44; A61F 5/448
(52) U.S. Cl. .................. 604/355; 604/327; 604/339
(58) Field of Search .................. 604/327, 331, 604/337, 338, 339, 341, 342, 348, 355, 385.19

(56) References Cited

U.S. PATENT DOCUMENTS

| 3,577,989 | A |   | 5/1971 | Anderson | 128/283 |
| 3,734,096 | A | * | 5/1973 | Millenbach | 128/283 |
| 3,804,093 | A | * | 4/1974 | Fell | 128/286 |
| 4,368,733 | A | * | 1/1983 | Sanidas | 128/283 |
| 4,445,898 | A | * | 5/1984 | Jensen | 604/337 |
| 5,312,384 | A | * | 5/1994 | Temple | 604/355 |

FOREIGN PATENT DOCUMENTS

| EP | 0 753 290 A |   | 1/1997 |   |
| GB | 1 078 588 A |   | 8/1967 |   |
| GB | 1 092 274 A |   | 11/1967 |   |
| GB | 2 116 849 A |   | 10/1983 |   |
| GB | 2 140 692 | * | 5/1984 | A61F/5/44 |
| JP | 08 117261 |   | 5/1996 |   |

* cited by examiner

Primary Examiner—John G. Weiss
Assistant Examiner—Michael Bogart
(74) Attorney, Agent, or Firm—Larry L. Huston; Jeffrey R. Moore; Leonard W. Lewis

(57) ABSTRACT

A faecal management device having a flange or abutting the perianal region of a wearer. The flange has an aperture therethrough. The aperture has a contour defined by two mutually perpendicularly oriented ellipses.

8 Claims, 9 Drawing Sheets

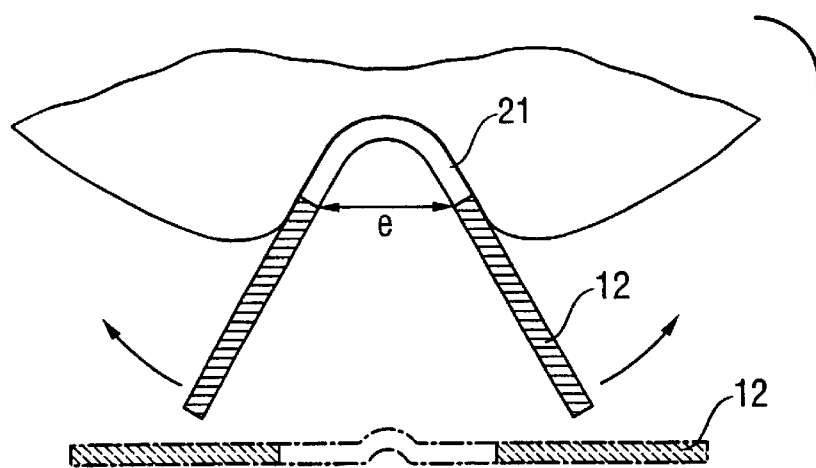
Fig. 4a
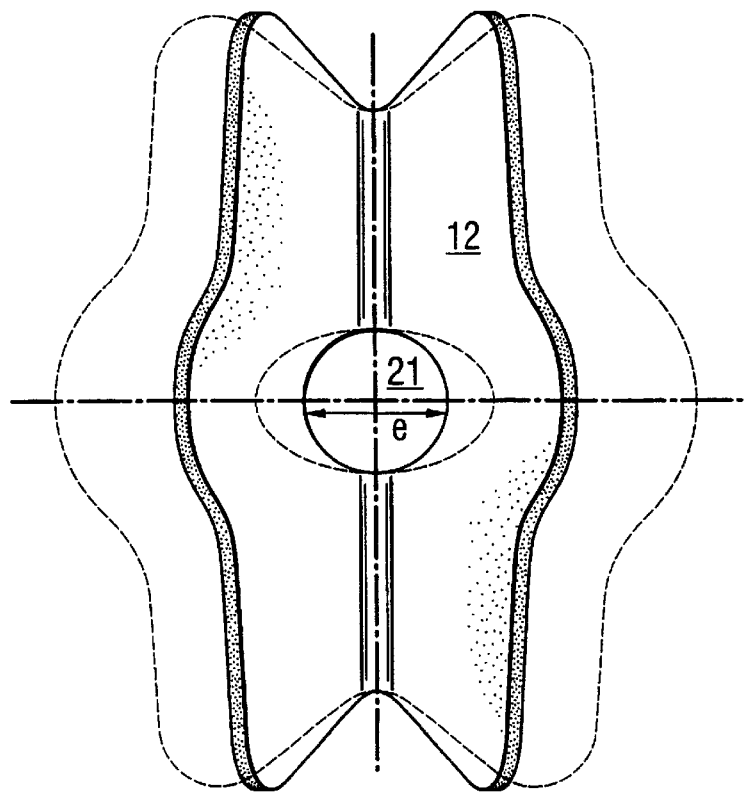
Fig. 4b
*Fig. 4*

ADHESIVE FAECAL COLLECTOR WITH OPTIMAL APERTURE

FIELD OF THE INVENTION

The present invention relates to faecal management devices for babies, children or adults, to be adhesively attached in a releasable manner to the perianal area of the wearer, said devices being particularly easy to put in place and providing a largely improved performance in collecting faecal matter.

BACKGROUND

Faecal management devices are known articles of manufacture that are designed to be worn principally by incontinence sufferers and in particular by bedridden patients. Such faecal management devices are attached to the perianal area of the wearer and are intended to entrap and immediately contain faecal material and other bodily discharges.

Such devices as they are mostly known today are constituted of a bag, at one extremity of which is positioned the aperture and the attachment device. Such bags are disclosed in, e. g. U.S. Pat. No. 3,577,989 and in U.S. Pat. No. 3,522,807.

A problem naturally associated with these devices is their secure attachment to the human body whilst allowing for the faecal matter to be safely contained within the bag. The approach which is mostly used in the field is to provide the device with a flange which surrounds an aperture and provide adhesive on the flange, which will stick to the perianal area. The aperture is to be brought in registry with the anal opening of a wearer and allows for the faecal matter to be contained in the bag.

U.S. Pat. No. 3,522,807 and U.S. Pat. No. 3,734,096 describe a circular aperture and an essentially circular, thus ring-like flange, which corresponds to the circular form of the sphincter muscle. U.S. Pat. No. 3,522,807 teaches that flexibility in the radial direction is beneficial to allow for the again radial enlargement of the sphincter muscle during defecation.

U.S. Pat. No. 5,593,397 discloses an approach of how to better adapt a ring-like flange surrounding a circular aperture to the anatomy of the wearer. A triangular portion of the flange is marked and those markings are intended to guide the caretaker in cutting out a triangle of the flange, e.g. by using scissors. Such an adaptation of the flange is thought to improve the fit of the faecal management device in the perineal area of the wearer.

U.S. Pat. No. 4,784,656 discloses a device provided with a small circular aperture, the flange of which is provided with markings to allow to cut out circular apertures with different diameters. This may be beneficial to better adapt the faecal management device to the anatomy of different wearers, however the use of a cutting device, such as scissors, has several drawbacks. The required cutting device may not be at hand, the cutting device may cause injuries to a person or damage to the faecal management device, the cutting is a time consuming process and furthermore may not be accurate.

Another solution to this problem is brought up in GB-A-2,116,849. Again, a flange having a circular outer contour is used in combination with a circular aperture. Here, the aperture and the flange are not concentric, so that the flange has a smaller width at one end and may better fit the perineal area of the wearer.

In U.S. Pat. No. 3,577,989 a device is disclosed, which has a non circular, in fact very long and small aperture. This device, however, is meant to entrap both, urine and faeces, and is as such a device of a different kind. The aperture thus being long enough to cover the urinary duct and the anal opening.

Kokai Patent Application No. HEI8 (1996) 117 261 discloses a faecal management device, where the aperture, which is meant to entrap faecal matter, is provided in the form of a hole or a slit. The hole or the slit is provided with thread, which can be used to close the hole or slit after the detachment of the device. This is thought as a means to diminish the malodour escaping from the aperture after detachment of the device. Said application does not give any detailed description of the nature of the aperture or of the flange. The fact, that the hole or slit can be closed with a thread discloses that the aperture does not have a constant or elastic form; the slit seems to be cut in a soft, flexible, somewhat flimsy material. Such a sealable aperture may be beneficial after the detachment of the faecal management device, however such an aperture seems to have disadvantages while the device is being used. A constant or elastic form of the aperture is much more beneficial to ensure that the aperture offers a sufficient area to entrap faeces in the device. Otherwise substantial portions of the faecal matter may not be entrapped in the bag. Furthermore such a constant or elastic form of the aperture avoids soiling of the flange; in particular the slit as described in said Kokai Patent Application seems likely to get soiled in the defecation process. Another alternative aperture is described in SE 8 104 934; however, such aperture forms which are chosen so that they depend on the form of the bag, are not desirable. Furthermore, if the aperture is not carefully chosen to be of a sufficient size and an appropriate form, substantial pressure on the flange may build up during the defecation process. Such substantial pressure can lead to the detachment of the adhesively secured device, obviously entailing the most unwanted consequences. The problem of unintentional detachment.

Besides and in connection with optimal attachment and anatomical fit, the proper placement of the device is a key issue in the field of faecal management devices. Total or substantial misplacement of the device will lead to a severe misfunctioning, in particular incomplete collection of faeces and leaking. The placement of adhesive faecal management devices is rendered difficult, inter alia by premature sticking of the device, i.e. sticking to the buttocks of a wearer before the intended placement position is reached. If the aperture of the faecal management device is not sufficiently in registry with the anal opening, substantial pressure on the flange of the device can build up in the defecation process, again leading to unintentional detachment.

If the misplacement of the device is recognized before use, the placement of the device is normally corrected, typically by the carer. The necessary detachment and reattachment of the device means an additional stress on the affected areas of skin of the wearer. Many wearers, who may make use of faecal management devices have a sensitive skin due to their age, whether very old or very young, and furthermore sometimes also suffer from skin irritations. Proper placement of the device in the first place is therefore highly desirable.

If the misplacement of the device is recognised before use, the placement of the device is normally corrected, typically by the carer. The necessary detachment and reattachment of the device means an additional stress on the affected areas of skin of the wearer. Many wearers, who may make use of faecal management devices have a sensitive skin due to their age, whether very old or very young, and furthermore sometimes also suffer from skin irritations. Proper placement of the device in the first place is therefore highly desirable.

In GB-A-2,116,849 it was attempted to provide an adhesive faecal management device which, among other properties, was easier to put in place on the patient. The solution brought up by GB-A-2,116,849 is, however, quite complex, involving individually removable sections of the release layer covering the adhesive layer on the flange surrounding the aperture, said sections having to be removed in a predetermined sequence in order to ensure optimum adherence. The removal of only a portion of the release paper in a first placement step allows in fact easier detachment and reattachment in the above described case of a noticed misplacement.

Another problem associated with faecal management devices is their behaviour after unintentional detachment and their handling after detachment. Since they regularly are a source of malodour and possibly of leakage, the area of the aperture should not be chosen larger than necessary for good performance. A means to close the aperture after use as described in Kokai Patent Application No. HEI8 (1996) 117 261 still cannot prevent malodour to escape before said thread is pulled and more importantly is of no help if a faecal management device is detached unintentionally.

Thus, considering the possible unintended detachment and the handling after use, a small aperture is desirable. Moreover, a small aperture prevents faecal matter from coming into contact with large areas of the wearer's skin. This reduces skin irritation problems. On the other hand, with regard to the importance of easy and proper placement of the device a large aperture may seem desirable. The man skilled in the art is faced with a similar problem in choosing the size and shape of the flange. The outer contour of the flange should not be too large to avoid bad anatomical fit of the device for some wearers, in particular in the perineal area of female wearers. On the other hand again, the flange has to provide the aperture of the required size and has to provide a sufficient area to be covered with an adhesive for the attachment of the faecal management device to the wearer. Secure attachment with a small flange area requires the use of an aggressive adhesive, which causes pain and possibly skin irritation, when the device is removed, whilst providing a larger surface area of the flange results in an excessively large flange which is difficult to handle, particularly with infants, or results in a smaller aperture.

All of the problems known in the art and mentioned are addressed by the present invention. Certain other substantial aspects of the performance and handling properties of faecal management devices have not been addressed in the prior art, however, they are successfully addressed by the present invention.

Firstly, the prior art does not teach, that the diameter of the aperture in the direction of the anal groove in the intended wearing position is of a particular importance with regard to the placement of the device. The placement of the device is more difficult in the longitudinal direction, i.e. along the anal groove of the wearer, than in the transversal direction. When placing the device between the buttock cheeks, the cheeks normally prevent severe misplacement in the transversal direction. However, no similar natural anatomical placing aid is provided in the longitudinal direction. Thus a placement somewhat out of registry with the anal groove is most likely in that direction. In an optimally designed faecal management device this fact should be reflected by the form and the size of the aperture. The prior art, as far as apertures of defined shapes are concerned, generally teaches only circular apertures.

Secondly, the prior art does not provide any teaching, as how to best choose the shape and the size of the aperture in the transversal direction. The flange is typically bent along an axis substantially parallel to the anal groove, when the device is worn. It is therefore important to consider, that when the device is worn the diameter of the aperture in the transversal direction effective for collecting faecal material is less than it would be on an unbent flange. Therefore whilst a circular aperture may, when correctly placed, offer a sufficient diameter to entrap faeces in the longitudinal direction, in real use will regularly offer a reduced and possibly insufficient diameter effective for collecting faecal matter in the transversal direction.

In attempting to overcome all the aforementioned problems relating to the prior art, it has now been found that adhesive faecal management devices can be designed which have excellent placement and functioning properties, through the selection of specific aperture parameters.

BRIEF SUMMARY OF THE INVENTION

This invention relates to a faecal management device (10) comprising a bag (11) and a flange (12). The flange (12) comprises adhesive (20) used to attach the device (10) to the perianal area of the wearer. The invention resides principally in providing an optimized shape of the aperture (21) of said device (10). One preferred embodiment of the invention is an aperture (21) whose contour is defined by one ellipse in the transversal direction; another preferred embodiment of the invention is an aperture (21) whose contour is defined by two ellipses whose major axes are perpendicular.

BRIEF DESCRIPTION OF THE DRAWINGS

FIGS. 4a and 4b are schematic views to illustrate the in-use position of a faecal management device. The effective transversal diameter is denoted as "e". FIG. 4a illustrates the bending of the flange which occurs in placing the device in the perianal area. FIG. 4b illustrates the difference in contour between the aperture of the flat flange and the projection of the aperture in the in-use position.

DETAILED DESCRIPTION OF THE INVENTION

Figure 1:
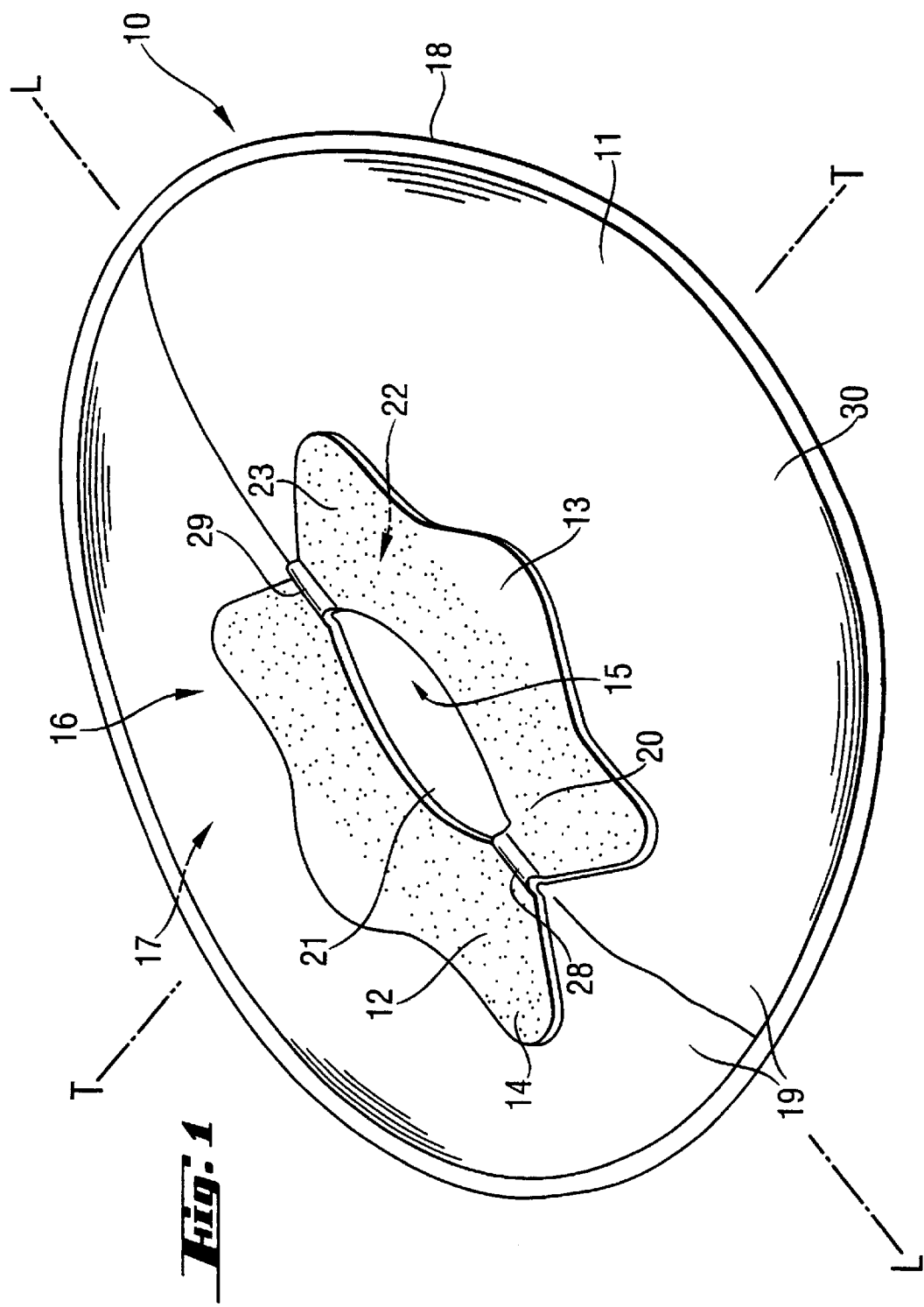
FIG. 1 is a perspective view of a preferred embodiment of the faecal management device. L denotes a longitudinal axis, T denotes a transversal axis.

The invention relates to a faecal management device (10) as shown in FIG. 1. The device (10) comprises a bag (11) and a flange (12).

Description of the Faecal Management Device as a Whole

Typically faecal management devices comprise a bag (11) having an aperture (21) and a flange (12) surrounding the aperture for preferably adhesive attachment to the perianal area of a wearer as visible from FIG. 1. Any faecal management device known in the art can be provided according to the present invention.

The bag (11) as used herein is a flexible receptacle for the containment of excreted faecal matter. The bag (11) can be provided in any shape or size depending on the intended use thereof, i.e. whether the device is intended for bedridden patients or active patients suffering from incontinence or requiring an artificial bowel or for infants. For example, elongated bags which are principally tubular or rectangular are typically utilised by bedridden patients and elderly incontinence sufferers. For more active wearers whether infants or adults, the faecal management device should preferably be anatomically shaped such that the device follows the contours of the body and can be worn inconspicuously by the wearer under normal garments.

Particularly, preferred shapes are flat circular type bags, cone shaped bags, truncated cone shaped bags and pyramidal or truncated pyramidal bags. In a most preferred embodiment of the present invention, the bag (11) has a substantially truncated cone shape. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag in-between the buttocks of the wearer and thereby ensure good contact between the flange and the skin of the wearer. For example, the bag (11) may be provided with a neck portion or conduit.

The bag (11) is preferably designed to provide sufficient volume for faecal material under a variety of wearing conditions, also when worn by a freely moving, i.e. not bedridden wearer. Sitting on the bag, for example, will result in a largely reduced volume in some areas of the bag. Thus, the bag is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag (11) is designed of sufficient strength to withstand rupture in use, also when pressure on the bag (11) is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibres or polymeric binders including natural fibres such as cellulose-wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapor such as water vapor in order to avoid the problem of entrapment and condensation of moisture vapor given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention the bag comprises two layers. Preferably the outer layer comprises a non-woven layer and the inner layer comprises a film. In yet another preferred embodiment of the present invention, the bag (11) comprises three layers, preferably one film and two non-woven layers . In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorchemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag (11) may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or crosslinked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner surface (15) of the bag (11). Any known techniques for securing absorbent material to nonwoven and film substrates may be used to secure the absorbent material to the inner surface (15) of the bag. The absorbent material may also be arranged to have any desired shape or configuration (e.g., rectangular, oval, circular, etc.).

As shown in FIG. 1 the bag (11) is provided with an aperture (21) whereby faecal matter is received from the body prior to storage within the bag cavity. The aperture (21) is surrounded by a flange (12) and may be provided in any shape or size, such as circular, oblong, heart shaped and may be symmetrical or asymmetrical.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering faecal matter.

The flange may be provided in any size depending on the wearer group for which the device is intended. Similarly the flange may be provided in any shape and preferably has a symmetrical shape preferably comprising a plurality of lobes (13)/(14).

The flange comprises a garment facing portion (22) and a wearer facing portion (23). In an preferred embodiment these are two large, substantially flat surfaces, however, the flange (12) may also comprise projections, a front projection (28) and/or a rear projection (29), designed to fit the perineal and/or coccygeal area of the wearer.

The flange (12) should be made of soft, flexible and malleable material to allow easy placement of the flange (12) to the perianal area. Typical materials include non-woven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimetres and a density of 5 to 250 $g/m^2$, more preferably 50 $g/m^2$. Other thermoplastic foam materials, or other suitable plastics sheet materials having the described properties of such foams (i.e., softness, pliability, stretchability, and contractability) might also be used. Preferably, the material of garment facing portion (22) of the flange (12) may extend into the defined aperture area so as to form a skirt or flap of material which prevents unintentional adhesion of the surface edges of the flange (12) defining the aperture (21) to one another during use.

According to the present invention the faecal management device (10) further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconized paper. The adhesive (20) can cover the entire wearer facing portion (23) of the flange (12) or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing portion (23) of the flange (12), so as to provide lobes (13)/(14) on either side of the flange (12) which are non-adhesive and can thereby serve to facilitate placement and removal of the device whilst avoiding contact with the adhesive. These lobes (13)/(14) are however preferably also covered by the release means. Before application of the faecal management device (10) to the skin of the wearer, the release means if present is removed.

According to the present invention any medically approved water resistant pressure sensitive adhesive may be used to attach the device to the perianal area of the wearer, such as hydrocolloid adhesives and hydrogel adhesives. Particularly effective adhesives in providing the desired adhesive properties to secure the flange to the skin of the wearer at the sensitive perianal area, whilst allowing for relatively painless application and removal, are formed from crosslinking polymers with a plastizicer to form a 3-dimensional matrix.

The adhesive (20) can be applied to the wearer facing surface portion (23) of the flange (12) by any means known in the art such as slot coating, spiral, or bead application or printing. Typically the adhesive (20) is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example, for faecal management devices (10) to be used for babies the amount of adhesive (20) may be less than for faecal management devices (10) designed for active adult incontinence sufferers.

Figure 2:
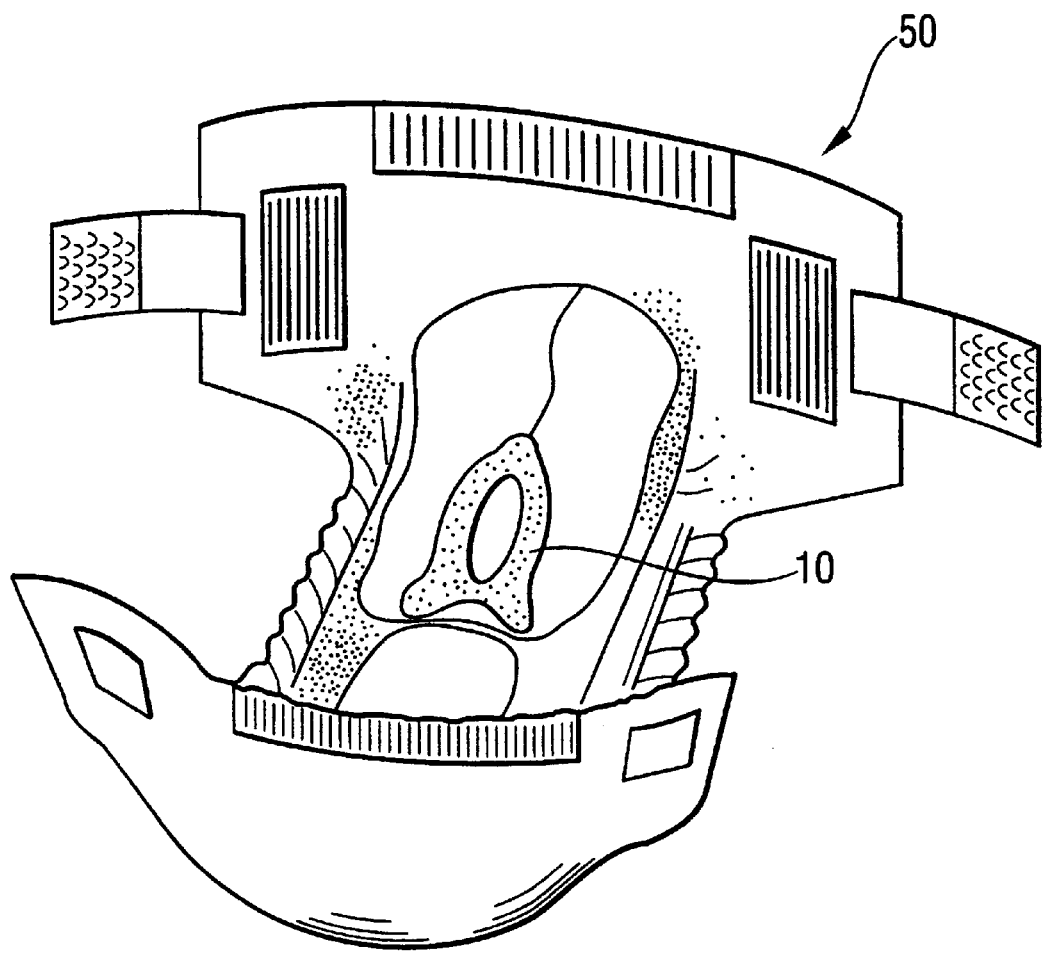
FIG. 2 is a perspective view of a diaper and a faecal management device, which can be worn in combination according to the present invention.

Detailed Description of a Diaper to be Worn in Combination with the Faecal Management Device The faecal management device (10) of the present invention has been found to be particularly useful and beneficial when used in conjunction with a garment, or diaper (50), preferably a disposable diaper—refer to FIG. 2. The faecal management device (10) is preferably first placed in the perianal area of the wearer before the disposable diaper (50) is applied. In particular, the diaper (50) is positioned over the faecal management device (10) and fastened in a conventional manner around the body of the wearer. It has been found that, in addition, to providing excellent separation between urine and faecal material, the combined faecal management device (10) and diaper (50) system actually reduces skin irritation, which may at times occur, especially since the group of typical wearers includes the very old, the very young and the unhealthy wearers. In effect, the presence of the faecal management device (10) permits the formation of a separation layer between the skin of the wearer and the diaper (50), i.e., a part of the absorbent core (58) of the diaper (10). The diaper (50) can be of the conventional type (an embodiment of which is described below although not a limiting example by any means) or can be adapted to contain in an effective and comfortable manner the faecal management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
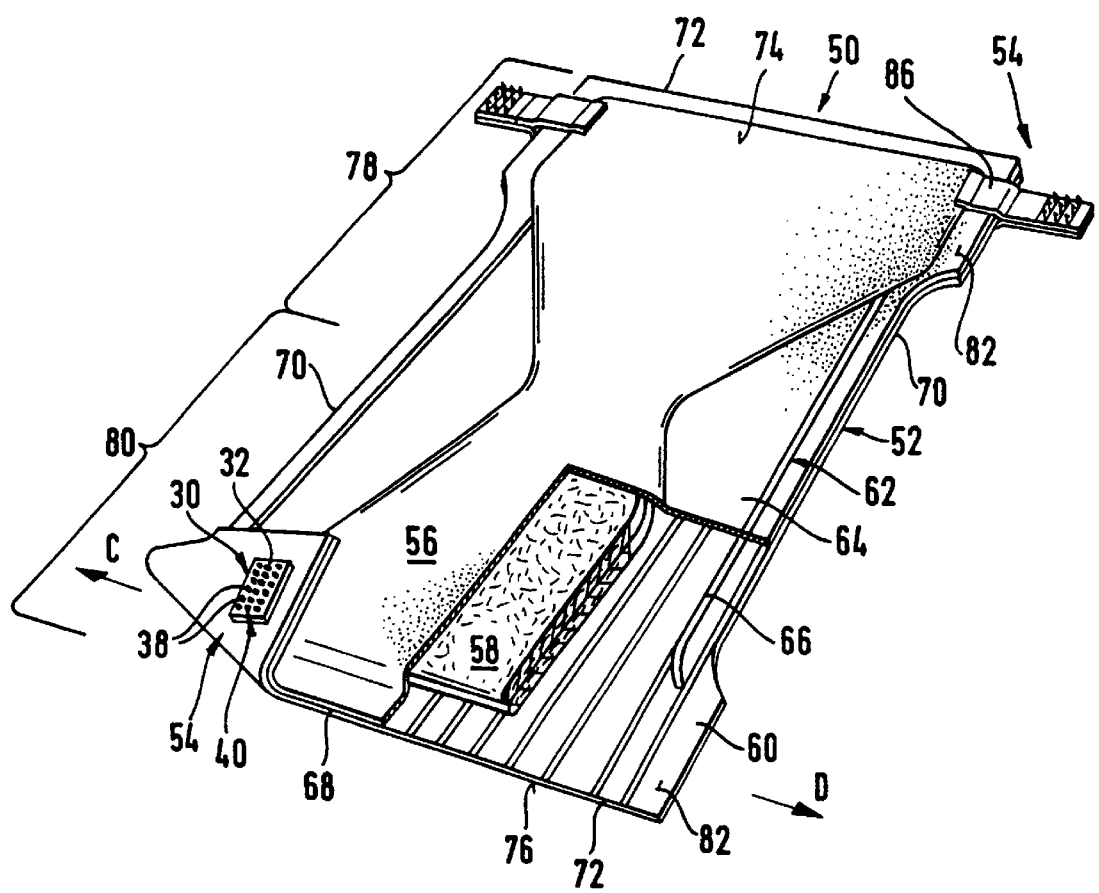
FIG. 3 is a partially cut-away perspective view of a diaper to be worn in combination with a faecal management device according to the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapours to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibres (for example, wood or cotton fibres) or from a combination of natural and synthetic fibres. Preferably, it is made of a material that isolates the skin of the wearer from liquids retained in the absorbent core (58).

There are a number of manufacturing techniques which may be used to manufacture the topsheet (56). For example, the topsheet (56) may be a nonwoven web of fibres. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

Detailed Description of the Aperture

To allow a more detailed and clear description of the device (10), in the following paragraphs firstly a few terms will be defined, as used herein.

Regarding in particular the flange (12) the longitudinal axis is to be understood as follows: The direction which is substantially defined by the anal groove in the intended wearing position shall define the longitudinal direction. The longitudinal axis is an axis in the longitudinal direction, which crosses the centre of the aperture (21). The most preferred indication of the intended wearing position is the presence of one or two projections (28) and/or (29) designed to fit the perineal and/or coccygeal area of the wearer, a less preferred indication of the intended wearing position is a fold in said flange (12) prior to use intended to be placed in parallel to the anal groove when placing the product. The longitudinal axis is typically also an axis of symmetry.

The transversal axis is an axis perpendicular to said longitudinal axis, which crosses the centre of the aperture (21).

Unbent is used with regard to the flange (12). The flange (12) is typically bent along a longitudinal axis to place it onto the perianal area of the wearer. In an unbent state the flange (12) is typically flattest.

Flat is used in the description of a three-dimensional object, such as the flange (12), if the object can be thought to be fully contained by a cuboid, characterized by three characterizing lengths, of which one first length is less than half of either of the two other characterizing lengths. If the object is flexible in shape, so that it may take several shapes without a substantial effect on its properties or damage, it is called flat if it is flat in one of said shapes. Such an flexible object is in its flattest shape if said first characterizing length is minimal.

The contour of the aperture (21) is defined by the inner periphery (25) of the flange (12). References to the contour of the aperture (21) are to be understood with reference to the unbent flange (12), unless otherwise stated. The contour of a flexible aperture (21) is to be understood as the form of the inner periphery (25) of the flange (12) when no outer forces are present which could affect the shape of the aperture (21) (apart from normally unavoidable forces such as gravity). If the aperture (21) is provided with a skirt, this skirt does not define the contour of the aperture (21).

Centre is used to describe a point of an object or a part of an object, which coincides with the centre of mass, if said object or part were of uniform density. Thus for the aperture (21), the centre is to be determined when the area within the contour of the aperture (21) is considered to be filled with a material of uniform thickness and density, when the flange (12) is unbent.

A diameter of the aperture (21) is the length of a line through the centre of the aperture (21), whose ends lie on the contour of the aperture (21), when the flange is unbent. The diameter of a flexible aperture (21) has to be measured when no outer forces are present which could affect the shape of the aperture (21) (apart from normally unavoidable forces such as gravity). The longitudinal diameter of the aperture (21) is measured along the longitudinal axis. The transversal diameter of the aperture (21) is measured along the transversal axis.

The major axis and the minor axis are characterising axes of an ellipses, the major axis being the longest axis of the ellipse and the minor axis being the longest perpendicular axis.

Longitudinally oblong is used with regard to an aperture (21) which has at least one local maximum in a diameter in at least one longitudinal section. A longitudinal section is defined by all directions extending from the longitudinal axis in either direction up to but excluding an angle of 45°. Transversally oblong is used if such a local maximum is present in the transversal direction. A local maximum is a maximum with regard only to the immediately adjacent diameters.

The faecal management device (10) is in the in-use position when the device (10) is attached to the perianal area of the wearer, so that the aperture (21) is registry with the anal opening of the wearer and the flange (12) is typically bent along the longitudinal axis.

The term Projection plane as used herein refers to one of the following planes: Faecal matter, which is to be collected by the faecal management device (10), will typically be transferred along a line from the centre of the anal opening of the wearer, to the centre of the aperture (21). Any plane perpendicular to said line is referred to as a projection plane. The term projection, as used herein, refers to a projection process, which yields an identical projection of an object, such as the aperture (21), onto any one of said projections planes.

Effective transversal diameter is to be understood as the length of a line in the transversal direction through the centre of the projection of the aperture (21) onto one of said projection planes, whose ends lie on the contour of the projection of the aperture (21) onto said projection plane.

The aperture (21) of the faecal management device (10) as used herein is to be understood as the part of the device (10) which receives faecal matter, which is then entrapped in the bag. The aperture (21) does not need to be open, when not receiving faecal matter. For example, the aperture (21) may be closed by a given mechanism, in particular after detachment.

It has been found, that the amount of excreted matter, which is successfully transferred to the bag (11) of the device (10) and hence does not leak, can be significantly improved by using an aperture (21) having different diameters in different directions, i.e. a non-circular aperture (21) (when the flange (12) is unbent). More particularly, it has been found beneficial to have larger diameters along the transversal or along the longitudinal axis or along both these axes, than in the directions in-between.

The main benefit of a transversally oblong aperture (21) is the improved functioning of the device (10) in its typical in-use position. When the device (10) is attached to the perianal area of the wearer, the flange (12) will typically be bent along the longitudinal axis, which is then is registry with the anal opening of the wearer. Faecal matter, which is to be collected by the faecal management device (10), will typically be transferred along a line from the centre of the anal opening of the wearer, to the centre of the aperture (21). The projection of the aperture (21) in its in-use position onto a plane perpendicular to said line determines if the aperture (21) is of sufficient size to transfer faecal matter of a given size. The projection of the contour of the aperture (21) in the in-use position differs from the contour of the aperture (21) of the unbent flange (12), as can be seen in FIG. 4. For example, a circular contour of the aperture (21) of the unbent flange (12) corresponds to an elliptical, longitudinally oblong contour of the aperture (21) in projection onto one of said projection planes, when the device (10) is in its in-use position. Thus a circular aperture (21) may not offer a sufficient effective transversal diameter for collecting faecal matter. On the other hand, a transversally oblong aperture (21) can be so configured as to have a circular projection onto one of said projection planes in the in-use position as depicted in FIG. 4.

This difference between the contour of the unbent flange (12) and the projection of the contour of the aperture (21) onto one of said projection planes is relevant to the diameter of the aperture (21) in the transversal but in not the longitudinal direction. Consequently, it is beneficial to choose the transversal diameter of the aperture (21) independent from the longitudinal diameter, thus allowing the aperture (21) to be non-circular. Reflecting the essentially circular contour of the anal opening, the projection of faecal matter onto one of said projection planes will be essentially circular. Therefore it is beneficial to have a transversally oblong aperture (21) on the unbent flange (12), so that the effective transversal diameter can be chosen to approximately correspond to the diameter efficient for collecting faeces in the longitudinal direction. For example, the aperture (21) can have the form of an ellipse with its major axis in the transversal direction, which is so chosen, that the projection of the ellipse onto one of said projection planes is circular, when the device (10) is in its in-use position. However, for reasons discussed below, it may also be beneficial to have an aperture (21) of a more complex form.

The main benefit of a longitudinally oblong aperture (21) is in the placement of the faecal management device (10). The correct placement of the device (10) involves bringing the aperture (21) in registry with the anal opening of the wearer. The chances for a misplacement in the transversal direction are less than the chances for a misplacement in the longitudinal direction. This is so, because the anal groove of the wearer supports the correct placement of the device (10) with regard to the transversal direction, but hardly with regard to the longitudinal direction. Thus an aperture (21), which is oblong in the longitudinal direction is desirable to allow for some misplacement in that direction, so that such misplacement will not result in the aperture (21) not covering the anal opening.

The aperture (21) as formed by the flange (12) has a defined resilient shape. It may yet be flexible to allow for the enlargement of the sphincter muscle during defecation without detachment of the device (10). Thus the shape of the aperture (21) may change when forces are present comparable to the forces involved in the movement of that muscle by an intended wearer. The aperture (21) is thought to be large enough to entrap faecal matter when the device is in the in-use position, so that the flexibility does not need to allow for enlargement of the aperture (21) under the pressure of faecal matter itself.

Figure 5:
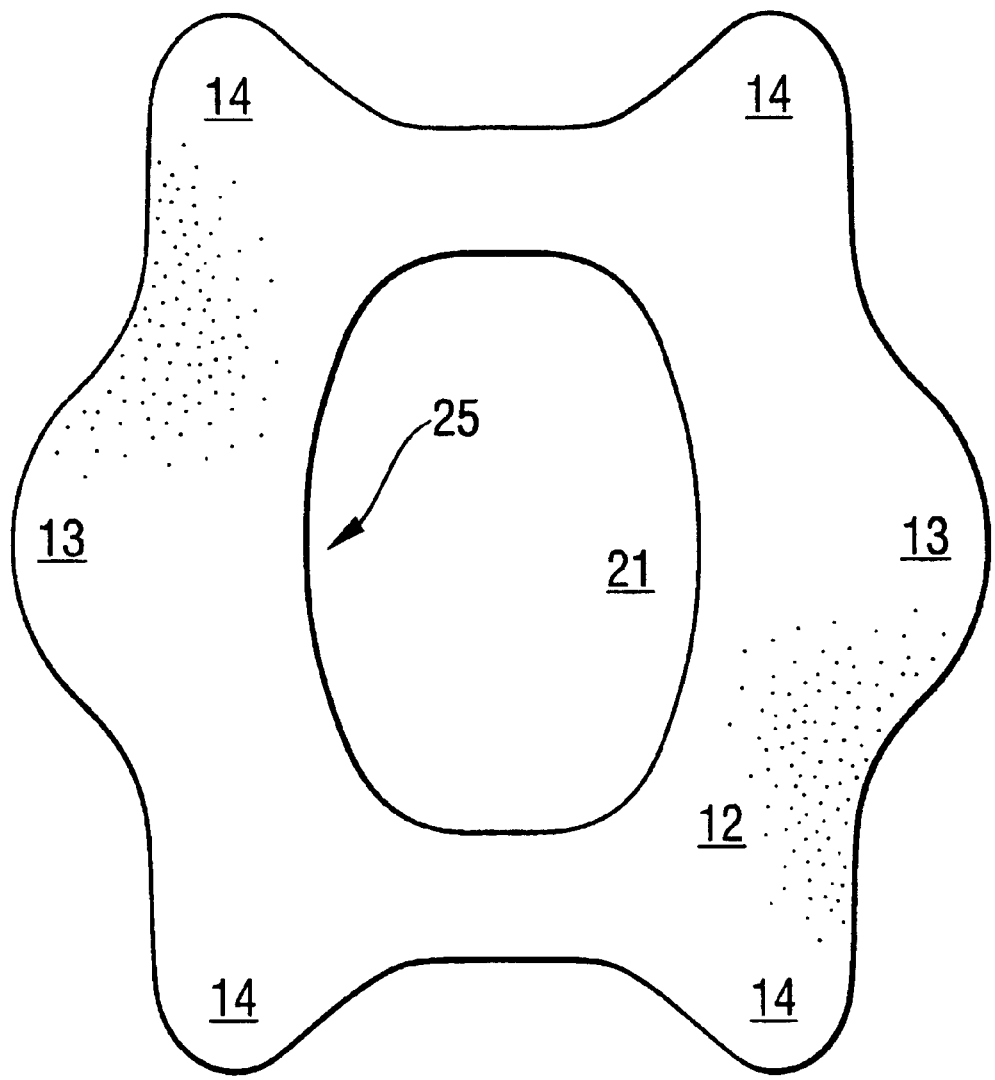
FIG. 5 is a top plan view onto a preferred embodiment of the aperture which is longitudinally oblong.
Figure 6:
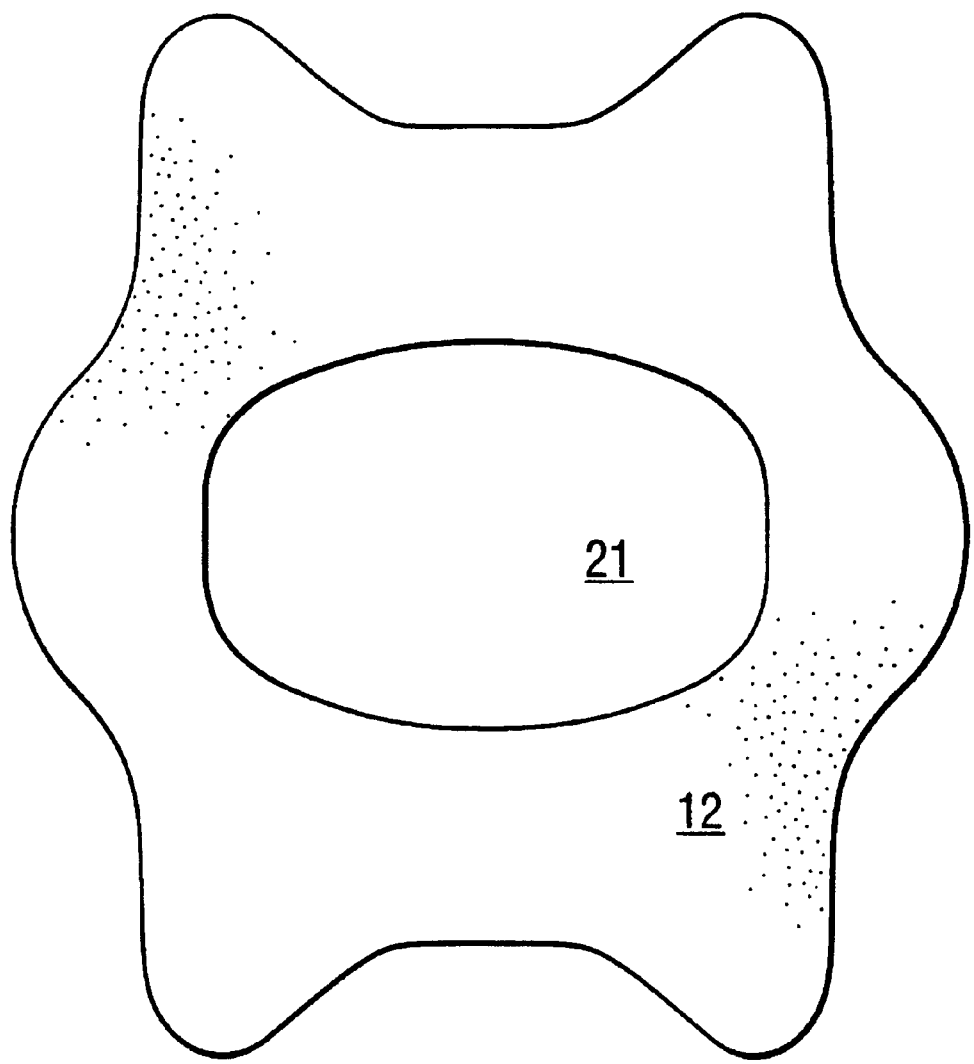
FIG. 6 is a top plan view onto a preferred embodiment of the aperture which is transversally oblong.

The aperture (21) may have a multitude of shapes, all of which are within the scope of the present invention. The choice of a particular shape will depend on the intended wearer group and using conditions. The aperture (21) may for example be elliptical in the longitudinal or in the transversal direction. The aperture (21) may also have an essentially elliptical form with flattened ends, e.g. to either side of the major axis as shown in FIG. 5 and in FIG. 6. Preferred flattened elliptical forms have a length along the major axis of 65% to 95%, more preferably around 80%, of the major axis of the corresponding full ellipse. Other flattened elliptical forms have a length along the minor axis of 65% to 95%, more preferably around 80% of the minor axis of the corresponding full ellipse. The flat portions preferably comprise a straight line. Elliptical forms of the aperture (21), which are flattened to either side of the major axis and to either side of the minor axis are also preferred.

Preferred elliptical apertures (21) have a ratio between the length of the major axis and the length of the minor axis from 1:0.05 to 1:0.9, more preferably said ratio is from 1:0.5 to 1:0.7. Preferred apertures (21) are also those which are oblong and close to elliptical, more preferably close to an elliptical aperture (21) of said preferred length ratios, without being strictly elliptical in a mathematical sense, thus being oval in a very broad sense. In particular, elliptical forms with flattened ends as described above are preferred embodiments of the present invention. For an ellipse with flattened ends, said length ratios are to be taken between the longest first diameter of the aperture (21) and the longest second diameter of the aperture (21) perpendicular to said first diameter, typically these are the longitudinal and the transversal diameters of the aperture (21).

The aperture (21) does not need to have any element of symmetry, however in a preferred embodiment the aperture (21) is symmetrical to the longitudinal axis, and in an even more preferred embodiment the aperture (21) is symmetrical to the longitudinal axis and to the transversal axis. The symmetry of the aperture (21) to the longitudinal axis reflects the substantial symmetry of the human body to the longitudinal axis (as roughly defined by the anal groove) and thus is typically beneficial for the good anatomical fit of the faecal management device (10), as well as for proper adhesion and complete collection of faecal material. The symmetry of the aperture (21) to the transversal axis may allow the faecal management device (10) to be placed to the perianal area of the wearer without ensuring a specific orientation regarding the perineal and coccygeal areas of a wearer. Said symmetries typically also allow the easier, cheaper and more accurate production of the flange (12) and may also ensure a more aesthetic appearance of the device (10).

Figure 7:
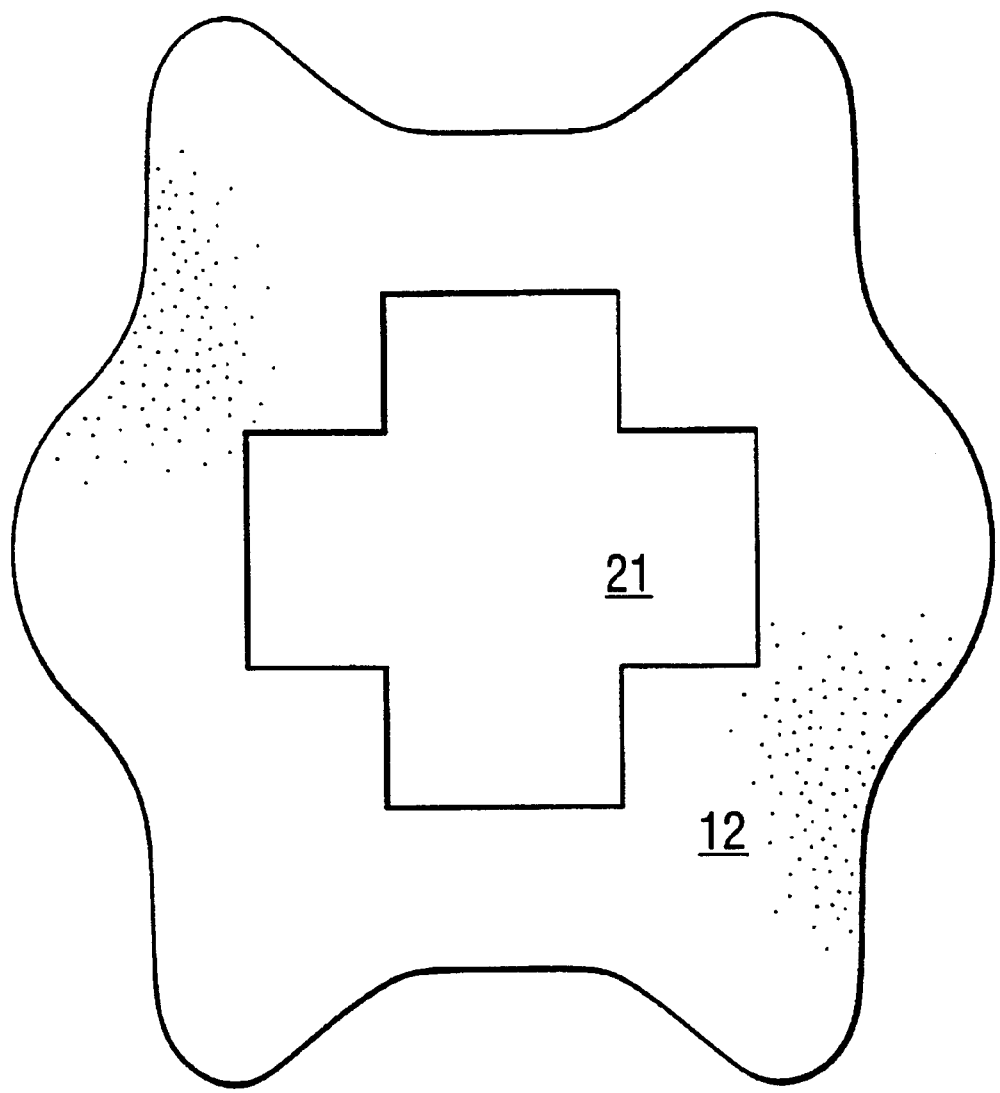
FIG. 7 is a top plan view onto a preferred embodiment of the aperture having the form of a cross.
Figure 8:
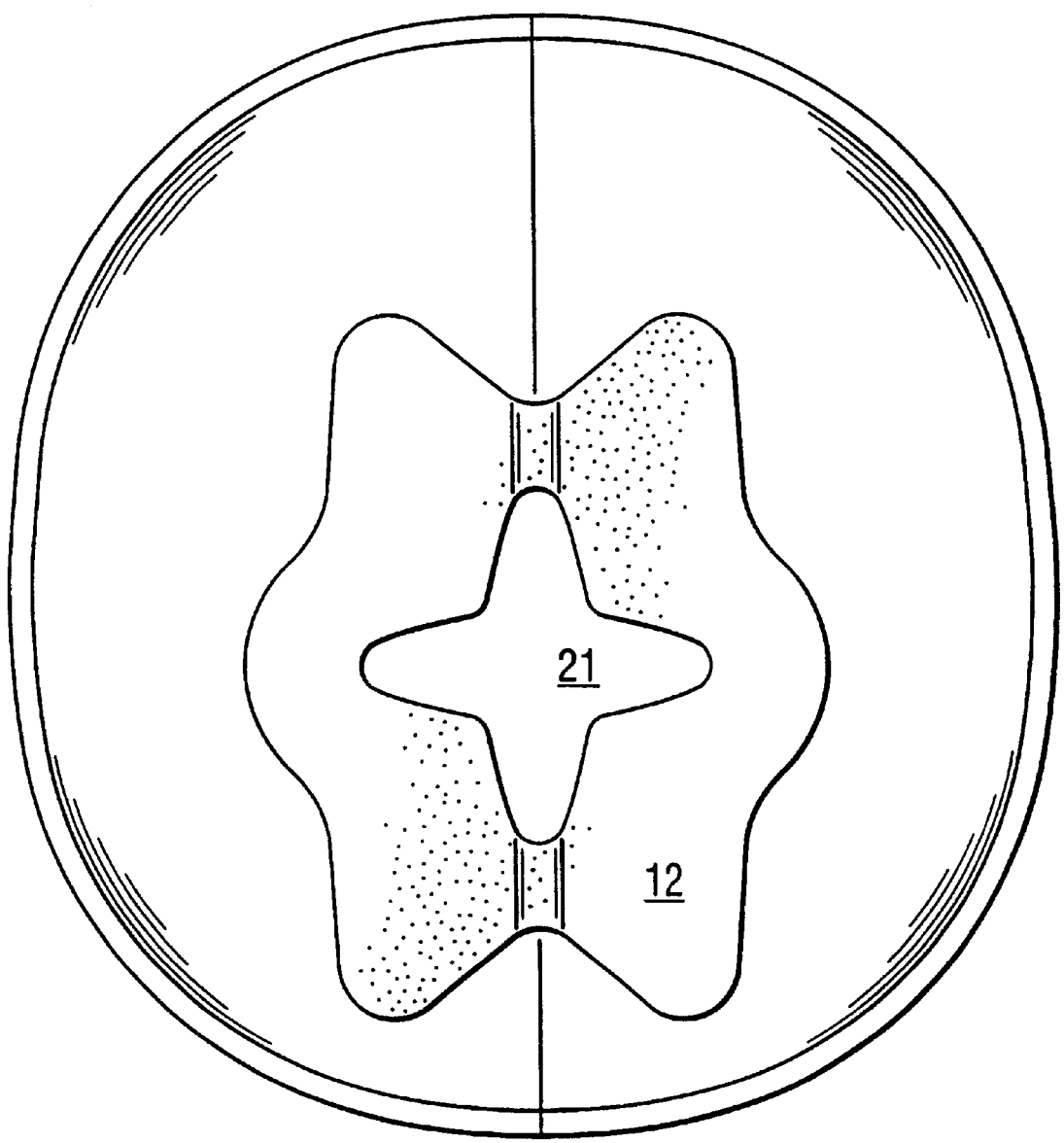
FIG. 8 is a top plan view onto a preferred embodiment of the aperture having a form based on two ellipses with perpendicular major axes.
Figure 9:
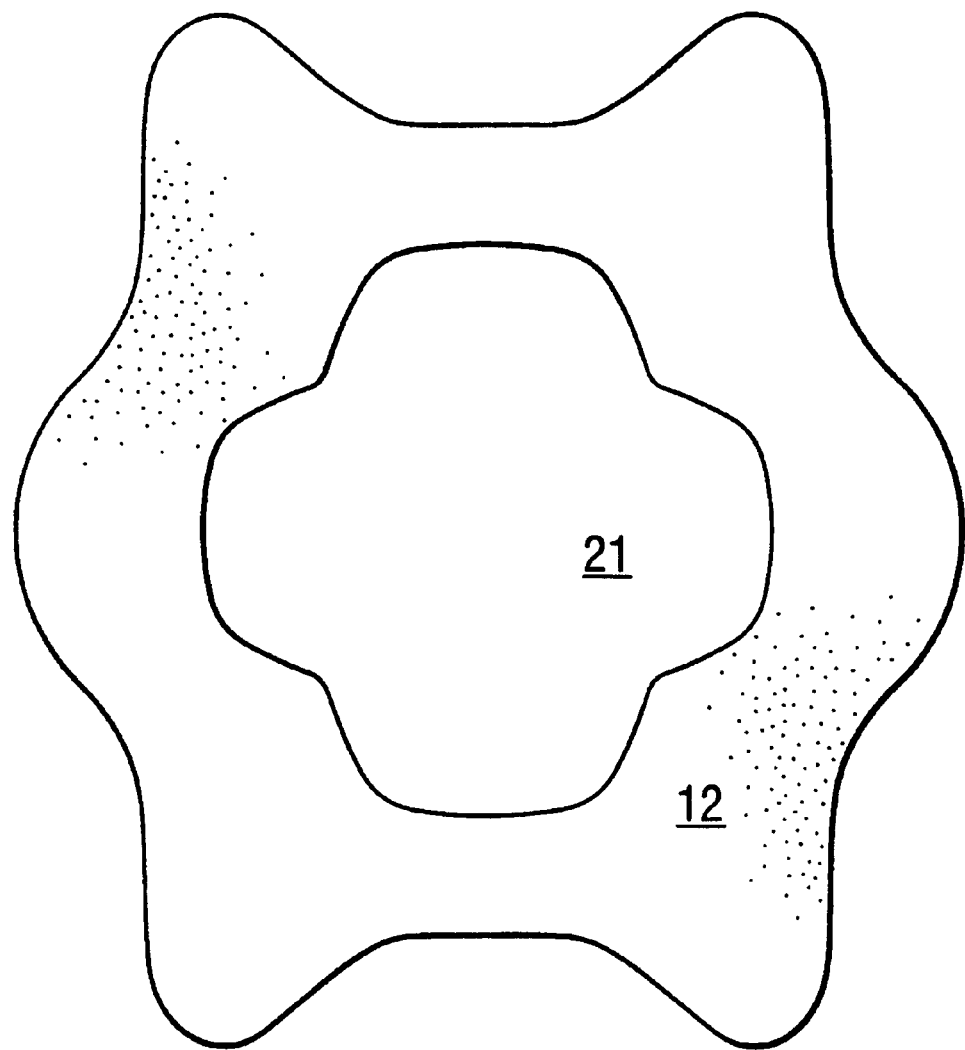
FIG. 9 is a top plan view onto a preferred embodiment of the aperture, which has a form based on two ellipses with perpendicular major axes and flattened ends to either sides of the two major axes.

The benefits of an aperture (21) which is transversally oblong and the benefits of an aperture (21) which is longitudinally oblong can be combined. Such a combination can be achieved by a variety of embodiments. For example, the aperture (21) may have some diameter measured in any direction between the longitudinal and the transversal direction which is shorter by at least 5% than the shorter of two first diameters (longitudinal and transversal). More preferably, the diameter of the aperture (21) under a degree of 45° to the longitudinal axis is at least 5% less, more preferably 20% less than the diameter measured in either the longitudinal or the transversal direction. For example, the aperture (21) may have a contour to form a cross like shape as seen in FIG. 7. More preferably, the aperture (21) has a contour which is defined by two ellipses with perpendicular major axes, as shown in FIG. 8. Yet more preferably, said ellipses have a length ratio between the major axis and the minor axis from 1:0.05 to 1:0.9, more preferably said ratio is from 1:0.5 to 1:0.7. Particularly preferred elliptical forms have flattened ends as shown in FIG. 9.

All the embodiments described herein have an aperture (21) as small as possible with regard to the optimal performance of the device (10) for particular wearer groups and uses. Thus, the risk of skin irritation due to contact of faecal matter with the skin of the wearer is as far as possible reduced. Furthermore it is a particular advantage of the apertures (21) described herein to provide large surface areas of the flange (12) close to the centre of the aperture (21) while not hindering the defecation process and thereby still allowing effective collection of faecal matter. The presence of such large areas of the flange (12) close to the centre of the aperture (21) is very beneficial, as it allows for a more secure attachment of the faecal management device (10) by adhesive provided on the wearer facing portion (23) of the flange (12).

The size of the aperture (21) should be chosen with regard to the typical faecal matter of the intended wearer group. It has been found that faecal matter of various consistencies and various wearer groups has a typical maximum calliper of 0.1 to 4.0 cm after defecation when projected onto said plane, the upper calliper limit being 2.0 cm for babies. This maximum diameter may have to be measured in the longitudinal or in the transversal direction or any direction in between.

The transversal diameter of the aperture (21) is to be chosen regarding the kind of faecal matter to be entrapped and regarding the considerations described above: To allow for a given faecal matter diameter in said projection plane, the aperture (21) has to be transversally larger in diameter when the flange (12) is unbent than said given faecal matter diameter. Preferably the transversal diameter of the aperture (21) is 100% to 500%, more preferably from 150 to 300% of the expected maximum faecal matter diameter of a particular wearer group. Even more preferably the aperture (21) has a transversal diameter of 3.0 to 8.0 cm, most preferably 4.0 cm.

The longitudinal diameter of the aperture (21) should preferably be chosen to allow for the effective functioning of the device (10) despite misplacement. It has been found that the misplacement of the device (10) in the longitudinal direction is typically up to 2 cm in either direction (coccygeal or perineal), mostly only up to 1 cm. Therefore, the longitudinal diameter should be chosen to allow for the expected faecal matter diameter and the expected device misplacement. Preferably the longitudinal diameter of the aperture (21) is form 1.0 cm to 8.0 cm, most preferably 4.0 to 6.0 cm.

Preferably, the longest diameter of the aperture (21) measured on any of the embodiments described above is at least 5 cm.

What is claimed is:

1. Faecal management device comprising a bag, said bag having an aperture, said aperture having an outer contour defined by the contours of two ellipses, a first ellipse and a second ellipse, each said ellipse having a major axis and a minor axis, said major axis of each said ellipse being substantially perpendicular to said major axis of said other ellipse, said bag further comprising a flange surrounding said aperture, said flange having a wearer facing portion and a garment facing portion opposed thereto for releasable attachment to the perianal area of a wearer.

2. Faecal management device according to claim 1, characterized in that wherein said major axis of said first ellipse is in the longitudinal or transversal direction.

3. Faecal management device (10) according to claims 2, wherein at least one of said first ellipse or said second ellipse has flattened ends.

4. Faecal management device (10) according to claim 1, characterised in that the material of said garment facing portion (22) of the flange extends into said aperture (21) so as to form a skirt.

5. Faecal management device (10) according to claim 1, characterised in that said aperture (21) has an axis of symmetry in the longitudinal direction.

6. Faecal management device (10) according to claim 1, characterised in that the longest diameter of said aperture (21) is at least 5 cm.

7. Faecal management device (10) according to claim 1, characterised in that the transversal diameter of said aperture (21) is from 3.0 to 8.0 cm.

8. Faecal management device (10) according to claim 1, characterised in that the longitudinal diameter of said aperture (21) is from 1.0 to 8.0 cm, preferably 4.0 to 6.0 cm.

* * * * *